United States Patent [19]

Rashkin

[11] Patent Number: 4,837,347

[45] Date of Patent: Jun. 6, 1989

[54] PROCESS FOR OXIDATION OF ETHYLENE TO ETHYLENE OXIDE

[75] Inventor: Jay A. Rashkin, Monticello, N.Y.

[73] Assignee: Scientific Design Company, Inc., Little Ferry, N.J.

[21] Appl. No.: 215,618

[22] Filed: Jul. 6, 1988

Related U.S. Application Data

[62] Division of Ser. No. 388,865, Jun. 16, 1982, Pat. No. 4,774,222.

[51] Int. Cl.$^4$ ........................................... C07D 301/10
[52] U.S. Cl. ..................................................... 549/534
[58] Field of Search ......................... 549/534; 502/347

[56] References Cited

U.S. PATENT DOCUMENTS 2,404,438  7/1946  Evans .................................... 549/534
4,168,247  9/1979  Hayden et al. ....................... 502/347
4,774,222  9/1988  Rashkin ................................ 502/347

Primary Examiner—Richard L. Raymond
Assistant Examiner—Ba Trinh
Attorney, Agent, or Firm—Kenneth H. Johnson

[57] ABSTRACT

A supported silver catalyst selective to the formation of ethylene oxide in the reaction of ethylene with molecular oxygen is made by depositing an amount of an alkali metal sufficient to depress the activity and selectivity of the silver catalyst below that of its alkali-free state and thereafter heating the alkali metal-containing catalyst in a substantially oxygen-free atmosphere to reactivate it. In one embodiment, a large amount of alkali metal is deposited which removes substantially all activity from the silver catalyst and then activity and selectivity for oxidation of ethylene to ethylene oxide is recovered and enhanced by heating the catalyst in a nitrogen atmosphere to a temperature above 400° C. for a sufficient period of time.

20 Claims, No Drawings

PROCESS FOR OXIDATION OF ETHYLENE TO ETHYLENE OXIDE

This Application is a division of Ser. No. 388,865 filed June 16, 1982 now U.S. Pat. No. 4,774,222.

PRIOR ART

The invention relates generally to the oxidation of ethylene to ethylene oxide over a supported silver catalyst. Such catalyst and processes are well known in the prior art. More specifically, the invention relates to an improved catalyst containing substantially greater quantities of promoting alkali metals than have been considered suitable heretofore and a process of preparation of such catalysts by which they may be activated to produce improved results.

Many patents show the use of supported silver catalysts for the oxidation of ethylene to ethylene oxide. For many years, promoting metals have been added to further improve performance, and in particular the alkali metals. The art in this field has been very extensive as may be seen by an lengthy review of these patents given in G.B. No. 2,043,481A. Such disclosures have been somewhat inconsistent in their teachings, as can be seen by comparing U.S. Pat. No. 2,238,474 in which sodium and lithium hydroxides were suggested as promoters and potassium and cesium were shown to act as poisons with U.S. Pat. No. 2,671,764 where rubidium and cesium sulfates were suggested as promoting compounds.

Although alkali metals were suggested generally in the earlier disclosures, it is generally true that more recent workers in the field have considered potassium, rubidium, and cesium as the preferred alkali metals. For example, see the series of patents to Nielson, et al. in which these materials were used in small amounts co-deposited with the silver, U.S. Pat. No. 3,962,136, U.S. Pat. No. 4,010,115, and U.S. Pat. No. 4,012,425. Still more recently the art has emphasized in obtaining synergistic combinations of the alkali metals. For example see G.B. No. 2,043,241A cited above, and U.S. Pat. Nos. 4,212,772 or 4,226,782. In addition to their use in the preparation of fresh catalysts, the alkali metals have been used to rejuvenate used catalysts, as shown in U.S. Pat. No. 4,033,903 and a group of patents assigned to Hoechst, A. G. including U.S. Pat. Nos. 4,123,385 4,177,169 and 4,186,106. The art teaches that the alkali metals may be deposited either before the silver is placed on the support (predeposited), at the same time the silver is deposited (co-deposited), or subsequent to deposition of the silver (postdeposited). Examples of these techniques are given in U.S. Pat. No. 4,207,210 (predeposited), and the group of Nielson, et al. patents mentioned previously (codeposited), and in U.S. Pat. No. 4,066,575, U.S. Pat. No. 4,248,740, and G.B. No. 2,045,636A (postdeposited).

The amount of alkali metal was suggested to be quite wide in the older art. It was often indicated that large quantities, e.g. up to several percent of an alkali metal could be used. More recently, the art generally has taught that small quantities of alkali metals produce the optimum effect no matter when the silver and the alkali metals were deposited, although Kilty in U.S. Pat. No. 4,207,210 related the optimum amount to the surface area of the support. An exception may be patents issued to ICI which teach the use of large amounts of sodium alone (British No. 1,560,480) and potassium in combination with smaller amounts of cesium and rubidium (U.S. Pat. 4,226,782). Generally, these amounts were limited to about 1000–1500 ppm by weight based on the total catalyst. For example, U.S. Pat. No. 3,962,136 in Example X shows that amounts of 1803 and 5621 ppm of cesium were detrimental. However, the art generally teaches that the optimum will be found in substantially lower quantities. Perhaps on the order of 50 to 500 ppm by weight. An apparent exception is found in Japanese published application No. 81-108533 assigned to Nippon Shokubai KK. That application contains examples in which large amounts of cesium are deposited on silver catalysts having relatively large surface areas and which are shown to have good performance. The application is primarily directed to a tratment with carbon dioxide at temperatures in the range of 100°–400° C.

Contrary to the apparent consensus of the prior art, it has now been found that very active and selective catalysts may contain large amounts of alkali metals. The amounts of alkali metals employed are substantially greater than those corresponding to the teachings of the most recent art and may be even larger than those previously suggested to be catalyst poisons. Surprisingly, although such large amounts of alkali metals may even be totally inactive when first deposited, as will be seen, it is possible through the preparation technique of this invention to convert these inactive catalysts into catalysts which are substantially improved in both activity and selectivity relative to an alkali-free silver catalyst.

SUMMARY OF THE INVENTION

A supported silver catalyst for the vapor-phase oxidation of ethylene to ethylene oxide is improved by including at least one alkali metal selected from the group consisting of sodium, cesium, rubidium, and potassium, preferably cesium, in a larger amount than is typical of the prior art and sufficient to depress the activity and selectivity of the silver catalyst below that of its alkali-free state. The depressed-activity catalyst is reactivated by heating at a temperature of at least 400° C., preferably in a substantially oxygen-free atmosphere. In a preferred embodiment, the performance is enhanced over that of the silver catalyst free of such alkali metals.

The catalyst of the invention will contain amounts of alkali metals considered heretofore to be excessive and which, in the absence of the heat treatment of the invention, would be less effective than a silver catalyst prepared in the same way, but containing no alkali metals. In some cases, the silver catalyst is substantially incapable of carrying out the desired oxidation of ethylene to ethylene oxide, until the heat treatment of the invention is carried out.

Silver will be deposited in amounts between 3–25% by weight on a support having a relatively low surface area, preferably in the range of 0.005–1.0 m$^2$/gm.

The amount of alkali metals(s) deposited will be at least 0.003 gm-equivalents per kg of finished catalyst and preferably will be less than about 0.3 gm-equivalents per kg of catalyst. The alkali metal may be deposited before, during, or after the deposition of silver on the support. The silver is given an activation treatment which comprises heating the silver-containing support in air at a temperature of 100° and 400° C. for a period of 1 to 8 hours. The activated catalyst, which actually may be substantially ineffective for oxidation of ethylene to ethylene oxide if the alkali metal is already present, is heat treated at temperatures substantially higher than those used for the "activation" of silver and is "re-activated" until its activity and/or selectivity are enhanced above that of a silver catalyst without such alkali metals. The temperature of the heat treatment will be at least 400° C., preferably 450° to 800° C., and especially 550° to 760° C. The time of treatment will range from 1 to 31 hours, preferably 2 to 29 hours, especially 3 to 27 hours. While the atmosphere preferably is substantially oxygen-free during the heat treatment, oxygen may be included to the extent that a detrimental effect is avoided. Broadly, the atmosphere should not exceed 50 vol % oxygen; preferably 0 to 30 vol %, especially 0 to 22 vol % may be used.

In another aspect, the invention comprises a process for the vapor-phase oxidation of ethylene to ethylene oxide in which a feed gas comprising ethylene and molecular oxygen at a temperature in the range of about 150° to 400° C. is passed over a supported silver catalyst prepared and reactivated according to the process described above.

DESCRIPTION OF THE PREFERRED EMBODIMENTS

Nomenclature

Certain terms are to be given a specific meaning for purposes of this disclosure. An "alkali-free silver catalyst" refers to one containing no added alkali metals, although some may be incidently present in the support before silver is deposited. The activity and selectivity of such a silver catalyst provides a reference point against which the treated catalyst is judged. To "depress" the activity and selectivity of an alkali-free silver catalyst is to reduce those properties by adding amounts of alkali metals which exceed those ordinarily used for a promoting effect. That is, the amount of alkali metal(s) added is defined as that initially deposited, before the heat treatment of the invention is carried out. At times the activity and selectivity can be reduced essentially to zero. To "reactivate" such a depressed silver catalyst means to increase its activity and selectivity above the depressed state. When the catalyst has an activity and/or selectivity equal to its base state, then it is said to have "recovered". When the catalyst activity and/or selectivity exceeds that of the "base" or "recovered" state, it is said to have been "enhanced".

Catalyst Composition and Preparation

Catalysts prepared in accordance with this invention contain about 3-25% by weight of silver, expressed as metal, deposited upon the surface of and throughout the pores of a porous refractory support. Silver contents higher than 25% by weight of total catalyst are effective but result in catalysts which are unnecessarily expensive. Silver contents, expressed as metal, of 7-20% based on weight of total catalyst are preferred, while silver contents of 8-15% are especially preferred.

The nature of the porous refractory support is not believed to be critical to the process of this invention, although it is known in general that relationships between support characteristics and performance exist.

Catalysts of good performance are obtained with supports comprising alumina, silica, mixtures of silica and alumina, silica-alumina, and silicon carbide, whether obtained from natural sources or synthetically prepared. Preferred supports are alpha-alumina-containing materials, optionally also containing up to 15-20 wt. % of silica. Especially preferred supports have an apparent porosity of at least 30% and preferably an apparent porosity in the range of 40-60%. Preferred supports also have a relatively low surface area, that is less than 30 sq. meters/gram, desirably less than 1.0 sq. meter/gram, and preferably in the range of 0.005-1.0 sq. meter/gram, especially 0.1-0.8 sq. meter/gram. Such surface areas are determined by the BET method [J. Am. Chem. Soc. 60, 309-16 (1938)]. Apparent porosities are determined by the mercury porosimeter method; see Drake and Ritter, "Ind. Eng. Chem. Anal. Ed.," 17, 787 (1945).

Supports having preferred characteristics are readily available from a number of commercial sources, e.g., from the Norton Company. Illustrative low surface, alpha-alumina-containing materials are commercially available from the Norton Company. Similar materials of like utility are commercially available from other sources.

| Designation | SA-5203 | SA-5552(1) | SA-5551(1) | CBO-6576(2) | SA-3235 |
|---|---|---|---|---|---|
| Alumina, wt % | 86.9 | 93.1 | 99.3 | 97.1 | 80.3 |
| Silica, wt % | 11.6 | 5.6 | 0.3 | 2.5 | 17.9 |
| Apparent porosity, % | 40-45 | 51-57 | 41-46 | 52.6 | 65 |
| % of pores with diam. in range of (in microns): | | | | | |
| <1 | | 5 | 5 | 10 | 1 |
| 1-10 | 20 | 87 | 87 | 70 | 27 |
| 10-100 | 70 | 8 | 8 | 20 | 22 |
| >100 | 10 | — | — | — | 50 |
| Surface area, sq. meters/gm | 0.02-0.08 | 0.3-0.37 | 0.15-0.35 | 0.2-0.35 | 2-10 |
| Pore volume, cc/gm | 0.21 | 0.31 | 0.25 | 0.28 | 0.61 |

(1)Norton Company
(2)Carborundum Company

For use in commercial ethylene oxide production applications, the supports are desirably formed into regularly shaped pellets, spheres, rings, etc. Desirably, the support particles used have "equivalent diameters" in the range from 2-12 mm. and preferably in the range of 4-10 mm. "Equivalent diameter" is the diameter of a sphere having the same external surface (i.e. neglecting surface within the pores of the particle) to volume ratio as the support particles being employed.

The silver is added to the support by immersion of the support into a liquid containing a compound or complex of silver, thereby enabling the silver-containing liquid to penetrate by absorption and/or capillary action into the pores of the support. A single immersion or a series of immersions, with or without intermediate drying, may be used. The concentration of the compound or complex of silver in the liquid will, in large measure, determine the silver content of the finished catalyst. To obtain catalysts having silver contents within the preferred range, suitable impregnating solutions will generally contain from 5-50 wt % of silver, expressed as metal, but supplied as silver compounds or complexes. The exact concentrations employed, of course, will depend upon, among other factors, the desired silver content, upon the nature of the support, and upon the viscosity of the liquid.

The impregnating medium is a liquid containing a compound or complex of silver, which is intended to encompass solutions and complexes of silver salts, both aqueous and non-aqueous, as well as molten silver salts, with or without additional diluents.

A common, suitable and readily prepared form of liquid containing a compound or complex of silver suitable for use in this invention is a molten silver salt of an organic acid, either alone or in combination with excess organic acid. For example, one may employ silver acetate, benzoate, oxalate, malonate, succinate, glutarate, and maleate. One may also employ hydroxysubstituted carboxylate anions such as, for example, the malate, lactate, citrate, glycolate, tartarate, etc., ions. Salts of hydroxy-substituted carboxylic acids and of dibasic acids are especially preferred. To enable relatively high silver levels on catalyst to be developed with a minimal number of immersions, anions containing more than 12 carbon atoms are generally not as desirable as those containing 12 carbon atoms or less. It is preferred to avoid carboxylate anions containing halo and/or sulfur substituents. Accordingly, illustrative of the especially preferred silver salts would be silver acetate, silver oxalate, silver citrate, silver lactate, silver benzoate, etc. Silver complexes such as the acetylacetonate or like complexes of silver with an organic moiety may also be used. Aqueous solutions of inorganic silver compounds such as silver nitrate and ammoniacal silver carbonate can be employed. Such solutions preferably also contain an organic compound such as the acids mentioned above, alkyl amines such as alkyl diamines and ethanolamine, and the like.

As indicated, the silver is deposited upon the support by immersion of the support into a liquid containing a compound or complex of silver until the solution has been absorbed into the pores of the support. Typical immersion times of from 1 to 60 minutes at temperatures of from 30° to 120° C. will usually suffice to achieve silver contents of as high as 10–15 wt %, as silver, with preferred systems wherein molten silver carboxylate salts with molten excess carboxylic acid, containing the order of 30 to 60% silver, expressed as metal, are used.

If aqueous solutions are employed, substantial vaporization of water should be avoided. Thus, the contacting is preferably conducted at super-atmospheric pressures of immersion temperatures are to exceed 95°–100° C., while atmospheric pressure is adequate if contacting temperature is to be in the range from ambient to about 95°.

In addition to the silver compounds or complex, the liquid in which the support is immersed can advantageously contain other ingredients. For example, in an alkaline earth metal promoter such as barium is to be incorporated into the catalyst, it is advantageously incorporated in this step by adding to the liquid a salt of the promoter metal which is soluble in the liquid in an amount sufficient to provide the desired promoter metal content in the finished catalyst. The anion associated with the promoter metal is not critical and the same or similar anions as those mentioned in connection with the silver compound or complex can be employed.

Additionally, because it is desired to maintain the silver in an oxidized state during this step, additives are frequently employed. Among the commonest additives useful for this purpose is hydrogen peroxide.

Avoidance of premature silver deposition, as well as enhancement of the ability of the silver compound or complex to permeate the support, is provided if the silver salt solution is maintained in an acid state, preferably by incorporation of free carboxylic acid, preferably that corresponding to the anion of the silver salt. Such liquids are readily made, for example, by admixing silver oxide with a carboxylic acid such as lactic acid and heating and causing the oxide to react with the acid to form the silver carboxylate, dissolved in excess carboxylic acid, liberating by-product water which need not be removed from the liquid.

Following such a procedure, and assuming that it is desired to employ silver lactate as the silver salt and to incorporate barium (supplied as barium acetate) as a promoter, a typically suitable liquid, after reaction of the silver oxide with lactic acid, would contain:

| Component | Wt % |
| --- | --- |
| Silver lactate | From 55 to 73 |
| Lactic acid | From 15 to 45 |
| Barium acetate | From 0.05 to 0.75 |
| Hydrogen peroxide (100% basis) | From 0 to 0.5 |
| Water | From 0 to 20 |

Liquids of the concentrations set forth above will readily provide finished catalysts having silver contents, expressed as metal, of from 8% to 15% based on weight of total catalyst and barium contents within the prefered range of from 100 to 1500 ppm, in a single immersion.

Following impregnation, the support is separated from any non-absorbed solution. Various means might be employed. Typically, the support is placed in a perforated container and lowered into a vessel containing the solution. The container is removed from the vessel and surplus solution is allowed to drain freely for 3 to 5 minutes or longer.

It is not considered to be critical to include alkali metal or metals at a particular time in the process of preparing the catalyst. The prior art catalysts ordinarily employ small amounts of alkali metals, with an optimum value being carefully achieved. With my catalyst, relatively large amounts of alkali metals are employed and the precise quantity used is not as important as with prior art catalysts. At least 0.003 gram equivalents per kg of finished catalyst will be used, preferably not more than about 0.3 gram equivalents per kg. The alkali metal or metals may be included prior to, during, or after the deposition of silver. It is convenient to include the alkali metal(s) an alkali metal compounds in the silver solution so that the alkali metal(s) and silver are co-deposited. When small amounts of alkali metal(s) are used as in the prior art, there are advantages to post-deposition of the promoting metal, since it can be done more precisely, however, the amount of metal deposited is less critical when large amounts are used.

The alkali metals of the periodic table include sodium, lithium, potassium, rubidium, and cesium. For purposes of the present invention, the latter three alkali metals are particularly preferred, especially cesium. Sodium will also be seen to be effective and to respond to the heat treatment of the invention. The alkali metal(s) will be supplied as metal compound(s) which can be dissolved in the silver-carrying solutions. The alkali metal(s) will be supplied as metal compound(s) which may be associated with various anions, as far example hydroxide, nitrates, formates and acetates, particularly acetates.

After the silver compound(s) or complex has been applied to the support, the catalyst is activated by heating the impregnated particles to a sufficient temperature to decompose the silver compound or complex, at least in part, to elemental silver in the presence of air. The dried particles may be gradually heated to a temperature in the range of about 300° to 400° C. and held at this temperature for a sufficient time to complete the activation. At about 350° C. this is readily accomplished in from 0.2 to 3.0 hours.

Although a catalyst "activation" is carried out, it is a characteristic of catalysts prepared according to the invention that they may not be very active for the oxidation of ethylene after this step. When already present in large quantities as with pre or co-deposition, the alkali metal suppresses both activity and selectivity of the silver catalyst and, as will be seen, in some cases the catalyst may appear to be not "activated", but deactivated by the alkali metal. If the alkali metal is post-deposited, the silver catalyst will have normal activity until the alkali metal is added. In any event, the amount of alkali metal used will be sufficient to depress the normal activity and selectivity compared to the silver catalyst containing no added alkali metal.

It has been discovered that such apparently deactivated catalysts cannot only recover the activity of an alkali-free silver catalyst, but they can be significantly enhanced in performance. This surprising result may be achieved by heating the relatively or completely inactive catalyst at temperatures much higher than are usually employed for activation of the silver and in an inert atmosphere to avoid oxidation and sintering of the silver particles, which would otherwise occur. The temperature of the heat treatment will depend to some extent upon the time the deactivated catalyst is heated, but it will be at least 400° C. and generally in the range of about 400° to 900° C., preferably 450° to 800° C., especially 550° to 760° C. The time required will range from 1 to 31 hours preferably 2 to 29 hours, especially 2 to 27 hours. Generally, it may be stated that the heat treatment will be carried out until the performance has stabilized at a desired level. The atmosphere employed during the heat treatment preferably is substantially oxygen-free. However, oxygen maybe included to the extent that a detrimental effect is avoided. Broadly the oxygen content should not exceed 50 vol %, preferably 0 to 30 vol %, and especially 0 to 22 vol % will be used. Various gases which are commonly available may be considered inert for purposes of the invention, such as nitrogen, argon, helium and the like. In one embodiment, an inert gas such as nitrogen is passed through the vessel containing the catalyst at a slight positive pressure to exclude oxygen during the treatment.

While the significance is not fully understood, it has been found that the structure of the catalyst differs from those found in conventional preparations. This appears to be true with respect to both the silver and the alkali metal. In conventional catalysts, characterized by activation at lower temperatures only up to about 350° C., the silver particles typically have an average equivalent diameter of about 0.1–0.5 microns. In catalysts prepared according to the invention, the silver particles have been sintered by the high temperature treatment and average about 0.5–1.0 microns. In conventional catalysts, the alkali metal is distributed uniformly over the surface. In contrast, with the new catalysts the alkali metal is agglomerated in what may be called "islands" distributed on both the support and the silver particles. After heat treatment, the alkali metal is found to have migrated into the support and silver particles. It is generally found also that less alkali metal is on the catalyst after the heat treatment and is believed to have migrated away from the catalyst as well as into it.

Catalysts prepared by the procedures described above may have improved performance for use in the production of ethylene oxide by the vapor phase oxidation of ethylene with molecular oxygen, as compared to catalyst containing only silver. Oxidation reaction conditions such as those previously known in the art may by employed. These usually involve reaction temperatures of about 150°–400° C., usually 200°–300° C., and reaction pressures in the range of from 0.5–35 kg/cm² gauge. Reactant feed mixtures usually contain 0.5–20% ethylene, 3–15% oxygen, with the balance comprising comparatively inert materials including nitrogen, carbon dioxide, methane, ethane, argon, and the like. Reaction modifiers, such as ethylene dichloride, may be included in minor amounts, typically 0.1 to 3 ppm by volume. Only a portion of the ethylene usually is reacted per pass over the catalyst and after separation of the desired ethylene oxide product and the removal of appropriate purge streams and carbon dioxide to prevent uncontrolled build-up of inerts and/or by-products, unreacted materials are returned to the oxidation reactor.

EXAMPLE 1

A sample of 200 gms of ¼" ring support type 5552 of the Norton Company is preheated and then dipped into 502 gm of lactic acid solution containing 32.5 wt % silver derived from $Ag_2O$, 0.39 wt % barium acetate, and 1.51 wt % cesium acetate. The impregnation is carried out for twenty minutes while the lactic acid solution is maintained at 85° C. The support is removed from the residual solution and drained. Then it is activated by heating in air for 2 hours at each of the following temperatures, 130° C., 200° C., 260° C., and 350° C. By analysis, the activated catalyst contains 16 wt % silver, 1000 ppm (wt) barium, and 5000 ppm (wt) cesium.

The activated catalyst is tested by placing 30 grams in a reactor of the type described by J. M. Berty in Chem. Eng. Prog. 70(5); 78(1974) and manufactured by Autoclave Engineers, Inc., Erie, Pa. The reaction products are recirculated in large quantities over the catalyst by an internal mixer. The fresh feed joins the recirculating reaction products and the mixture passes through the catalyst. The products of the reaction are withdrawn in an amount equivalent to the incoming feed. Owing to the presence of reaction products, the selectivity to the production of ethylene oxide is somewhat lower than when a plug-flow tubular reactor is used.

After 125 hours exposure to 200 liter/hr of a feed gas containing 14.1 vol % ethylene, 6.8 vol % oxygen, 5.7 vol % carbon dioxide, and 73.4 vol % nitrogen, along with 0.25 vol. ppm ethylene dichloride moderator, the activated catalyst showed no production of ethylene oxide at a temperature of 279° C. Similar samples of catalysts containing about 10,000 and 20,000 wt ppm of cesium also were found completely inactive. By way of comparison, a commercial catalyst prepared in a similar manner, but containing no cesium converted 10.5% of the ethylene with a selectivity of 69.9% to ethylene oxide with the same feed gas at a temperature of 235° C.

A second sample of the activated catalyst is placed in a 25 mm i.d. tubular reactor and heated for 5 hours at 700° C. and 1.41 kg/cm² gauge while 75 cc/min of nitrogen is passed over it. After the heat treatment the catalyst is loaded into a Berty reactor and tested under the same conditions as the untreated sample. After 175 hours 10.1% of the ethylene is being converted, with a selectivity of 70.3% to ethylene oxide at a temperature of 261° C. It will be recalled that, except for the operating temperature, the catalyst performance approximates that of the commercial catalyst previously tested.

A third sample of the activated catalyst, which had received a first heat treatment as described above, is heated a second time for 22 hours at 715° C. and 3.5 kg/cm² gauge while 3 liter/min of nitrogen is passed over it. After the second heat treatment the catalyst is tested as before and after 436 hours 9.7% of the ethylene is being converted with a 76% selectivity to ethylene oxide and at temperature of 235° C. A substantial improvement over the performance of the commercial catalyst is achieved by the heat treatment.

It is noted that while the activated catalyst contained about 5000 wt ppm of cesium, the second sample contained about 4800 wt ppm and the third sample about 4500 wt ppm. Other evidence indicates that some cesium had migrated from the catalyst, however, the surprising recovery and enhancement of activity and selectivity relative to the initial sample (which appeared completely inactive) is not attributed to the mere loss of about 10% of the cesium. Another sample prepared in a similar manner with 4100 wt ppm cesium after activation also was completely inactive. It also recovered and achieved enhanced activity and selectivity when given the two-step heat treatment described above. It is presumed that the loss of cesium has an effect on the composition and structure of the silver catalyst.

EXAMPLE 2

A series of catalysts are prepared by the methods of Example 1 having about 15 wt % silver, 1000 wt. ppm barium, and varying amounts of sodium and potassium. After activation the catalysts are tested in a Berty reactor of the type discussed above.

The catalysts are then heat treated by heating 100–400 gm samples for 3 hours at 720° C. and 0.2 kg/cm² gauge in a muffle furnace retort while 75 cc/min of nitrogen is passed over them. The first heat treatment is followed by a second treatment for 11 hours at 590° C. under the same conditions as the first.

The catalysts are tested with a feed gas containing 14.1% $C_2H_4$, 6.8% $O_2$, 5.7% $CO_2$, and 73.4% $N_2$ with 0.25 wt. ppm ethylene dichloride as a reaction modifier. The following results were obtained after the catalysts had reached a stable operation and compares the performance before and after heat treatment.

TABLE A

| Catalyst No. | Alkali Metal wt. ppm | | | Reactor Temp °C. | | Conversion of $C_2H_4$(%) | | Selectivity to EO(%) | |
|---|---|---|---|---|---|---|---|---|---|
| | before | after | type | before | after | before | after | before | after |
| 1 | 4000 | 3068 | Na | N/A | 242 | N/A | 10.1 | N/A | 72.0 |
| 2 | 4000 | 2731 | K | N/A | 242 | N/A | 10.1 | N/A | 72.5 |
| 3 | 694 | 267 | Na | 239 | 228 | 9.4 | 10.4 | 74.6 | 70.3 |
| 4 | 1177 | 322 | K | 283 | 235 | 1.2 | 9.8 | 64.5 | 70.9 |

It will be noted that catalysts 3 and 4 contain Na and K equivalent to about 4000 wt ppm of cesium or about 0.03 gm-equivalents per kg of finished catalyst.

The positive reactivating effect of heat treatments according to the invention is shown in the following test results for catalysts made according to the methods of Example 1 with differing amounts of cesium and variations in the heat treatment.

EXAMPLE 3

When the catalyst contains a smaller amount of cesium which does not completely inactivate the silver catalyst, an effect of the heat treatment is still observed, as will be seen in the following data(1).

| Catalyst | Cesium wt. ppm | Reactor Temp. °C. | % Conv. $C_2H_4$ | % Sel. to EO |
|---|---|---|---|---|
| 5(2) | 242 | 222 | 10.2 | 70.4 |
| 5 comp(3) | 240 | 230 | 9.3 | 75.9 |

(1) Feed gas composition 14.1% $C_2H_4$; 6.8% $O_2$; 5.7% $CO_2$, 73.4% $N_2$ and 0.25 ppm ethylene dichloride.
(2) Catalyst prepared as in Example 1 but initially containing 500 wt. ppm cesium. Heat treated for 3 hours at 720° C. and then for 11 hours at 605° C., both at 0 2 kg/cm² gauge with 75 cc/min flowing over a 400 gm. sample.
(3) Catalyst on same support, but given no heat treatment, containing 240 wt. ppm cesium.

The catalyst which has been heat treated appears to be somewhat more active than the comparable catalyst (the reactor temperature is lower to achieve the same yield of ethylene oxide), but less selective to the formation of ethylene oxide.

EXAMPLE 4

Although preferred, the heat treatment need not be carried out in two steps. A single treatment may be used. In this example a catalyst prepared according to Example 1 and containing 4,000 ppm cesium after heat treatment at 640° C. for 8 hours in a nitrogen atmosphere as previously described is tested with a feed gas containing 14.1% $C_2H_4$, 6.8% $O_2$, 5.7% $CO_2$, and 73.4% $N_2$ with 0.25 ppm ethylene dichloride as a moderator. The reactor is a once-through tubular reactor heated by a fluidized sand bath. The results are compared with the standard catalyst of Example 3, containing about 240 wt. ppm cesium but having received only an activation in air and no heat treatment according to the invention.

| Catalyst | Cesium wt. ppm | Reactor Temp. °C. | % Conv. $C_2H_4$ | % Sel. to EO |
|---|---|---|---|---|
| 6 | 4000 | 273 | 15.2 | 70.5 |
| 6 comp | 240 | 228 | 13.9 | 77.7 |

The single heat treatment has left catalyst 6 somewhat less active and selective than the standard catalyst 6 comp., but since catalyst 6 without heat treatment has essentially no activity under conditions normally suitable for oxidation of ethylene (see Example 1), it is clear that much of the desired performance has been regained.

EXAMPLE 5

While temperatures above 500° C. are preferred, the heat treatment may comprise periods of time at lower temperatures. A catalyst originally containing 4100 wt. ppm Cs was prepared as in Example 4 and given two periods of heat treatment following air activation of the silver in the usual manner. For 3 hours at 400 gm. sample of catalyst is held at 720° C. and then for 22 hours at 400° C. while 75 cc/min of nitrogen is passed over the catalyst. After completion of the heat treatment the catalyst is tested in a Berty (i.e. recirculation-type) reactor, with the following results:

| Catalyst | Cesium wt. ppm | Reactor Temp. °C. | % Conv. $C_2H_4$ | % Sel. to EO |
|---|---|---|---|---|
| 7 | 3346 | 236 | 9.8 | 73 |
| 7 comp | 240 | 232 | 9.8 | 75.2 |

It can be seen that the heat treated catalyst is slightly less active and selective than the standard catalyst, but that the two step heat treatment has substantially improved the catalyst performance.

EXAMPLE 6

Much larger amounts of alkali metals can be used if desired. As will be seen in the following results. Catalysts are prepared according to the procedures of Example 4 and containing 20,000 wt. ppm cesium (catalyst 8) and 40,100 wt. ppm (catalyst 9). After air activation of the silver the catalysts are heat treated 720° C. for 3 hours and then at 590° C. for 11 hours while exposed to a flow of 75 cc/min of nitrogen for each sample of 400 grams. The heat treated catalysts are tested in a Berty reactor with a feed gas having the same composition as in Example 4 with the following results:

| Catalyst | Cesium wt. ppm | Reactor Temp. °C. | % Conv. $C_2H_4$ | % Sel. to EO |
|---|---|---|---|---|
| 8 | 17,750 | 280 | 7.1 | 61.6 |
| 8 comp | 240 | 230 | 9.3 | 75.9 |
| 9 | 37,847 | 350 | 3.4 | 7.1 |
| 9 comp | 240 | 231 | 9.0 | 78.6 |

It will be seen that catalyst 8 recovered a substantial amount of activity and selectivity that catalyst 9 showed some recovery, but was still inactive, suggesting that the heat treatment is not able to overcome the adverse effect of gross amounts of cesium.

EXAMPLE 7

Although a substantially oxygen-free atmosphere is preferred for the heat treating of catalysts according to the invention, exposure to oxygen may be employed, as illustrated by the following data. A catalyst prepared according to Example 1 containing about 4000 ppm of cesium as prepared was heat treated by exposure for 5 hours at 700° C. in the presence of nitrogen in the manner previously described followed by an additional 5 hours at 600° C. in the presence of air. When tested with a feed gas containing 14.1 vol % ethylene, 6.8 vol % oxygen, 5.7 vol % carbon dioxide, 73.4 vol % nitrogen and 0.5 ppm ethylene dichloride, the following results were obtained.

| Catalyst | Cesium wt. ppm | Reactor Temp. °C. | % Conv. $C_2H_4$ | % Sel. to EO |
|---|---|---|---|---|
| 10 | 3427 | 247 | 9 | 77.2 |
| 10 comp | 240 | 231 | 9 | 78.6 |

A catalyst containing 4000 wt. ppm cesium would be expected to be substantially inactive for the production of ethylene oxide (see Example 1). Heat treatment according to the invention produced a catalyst having good performance, close to that of a standard low-cesium catalyst which received no heat treatment.

The invention claimed is:

1. In a process for oxidation of ethylene with molecular oxygen to produce ethylene oxide at a temperature in the range of about 150° to 400° C. over a supported silver catalyst wherein the improvement comprises a catalyst in which a support is impregnated with a solution of a silver compound and activated by heating in air and includes at least one alkali metal selected from the group consisting of sodium, cesium, rubidium and potassium in an amount sufficient to depress the activity and selectivity of said alkali-containing silver catalyst relative to an alkali-free catalyst after activation and thereafter heat treating said alkali metal-containing catalyst at a temperature of at least 400° C. for a period of time sufficient to reactivate said depressed catalyst.

2. The process of claim 1 wherein said alkali metal-containing catalyst is heat treated until it recovers the performance of an alkali metal-free catalyst.

3. The process of claim 2 wherein said alkali metal-containing catalyst is heat treated until it achieves enhanced performance relative to an alkali metal-free catalyst.

4. The process of claim 1 wherein said support has a surface area of 0.005–1.0 $m^2/gm$.

5. The process of claim 1 wherein said alkali metal is at least 0.003 gm-equivalents per kg of finished catalyst.

6. The process of claim 5 wherein said alkali metal is between 0.003 and 0.3 gm-equivalents per kg of finished catalyst.

7. The process of claim 1 wherein said alkali metal is cesium.

8. The process of claim 1 wherein said alkali metal is co-deposited with said silver.

9. The process of claim 1 wherein said silver catalyst is activated by heating to a temperature of about 100° to 400° C. in an oxygen-containing atmosphere for a period of 1–8 hours prior to said heat treatment.

10. The process of claim 1 wherein said heat treatment is carried out at a temperature within the range of about 450° to 800° C.

11. The process of claim 10 wherein said heat treatment is carried out at a temperature within the range of about 550° to 760° C.

12. The process of claim 1 wherein said heat treatment is carried out in a substantially oxygen-free atmosphere.

13. The process of claim 1 wherein said heat treatment is carried out in an atmosphere containing no more than 50 vol % oxygen.

14. The process of claim 13 wherein said heat treatment is carried out in an atmosphere containing about 0 to 30 vol % oxygen.

15. The process of claim 14 wherein said heat treatment is carried out in an atmosphere containing about 0 to 22 vol % oxygen.

16. A process for the vapor phase oxidation of ethylene to ethylene oxide comprising of contacting ethylene in vapor phase at a temperature in the range of 150° to 400° C. with a catalyst prepared by
 (a) impregnating a support with solution comprising an amount of a silver compound sufficient to provide 3–25 wt percent silver and an amount of a cesium compound sufficient to provide 0.003 to 0.3 gm-equivalents of cesium per kg of finished catalyst and separating the impregnated catalyst from said solution;

(b) activating said impregnated catalyst by heating to a temperature of about 100° to 400° C. in an oxygen-containing atmosphere for a period of 1-8 hours to produce a catalyst having depressed activity and selectivity;

(c) heat-treating said activated catalyst of (b) in an substantially oxygen-free atmosphere at a temperature of at least 400° C. for a period of time sufficient to reactivate said depressed catalyst.

17. The process of claim 16 wherein said cesium-containing catalyst is heat treated until it recovers the performance of an alkali metal-free catalyst.

18. The process of claim 16 wherein said cesium-containing catalyst is heat treated until it achieves enhanced performance relative to an alkali metal-free catalyst.

19. In a process for the vapor phase oxidation of ethylene to ethylene oxide comprising (a) contacting ethylene in vapor phase at a temperature in the range of 150° to 400° C. with a supported silver catalyst prepared by a process in which a support is impregnated with a solution of a silver compound and activated, the improvement comprising including at least one alkali metal in an amount between 0.003 and 0.3 gram-equivalents per kg of finished catalyst, and thereafter heat-treating said alkali-metal-containing catalyst at a temperature of at least 400° C. in an inert gas atmosphere.

20. In a process for the vapor phase oxidation of ethylene to ethylene oxide comprising (a) contacting ethylene in vapor phase at a temperature in the range of 150° to 400° C. with a silver catalyst having silver deposited on a porous inorganic carrier in conjunction with at least one reaction accelerator selected from the group consisting of alkali metals to be used for the production of ethylene oxide, the improvement comprising the steps of depositing silver on the porous inorganic carrier in conjunction with at least one reaction accelerator selected from the group consisting of alkali metals thereby preparing an activated silver catalyst and subsequently subjecting said silver catalyst to a high-temperature treatment at a temperature greater than 400° C. in an inert gas atmosphere.

* * * * *